(12) United States Patent
Tatsumi et al.

(10) Patent No.: US 7,678,817 B2
(45) Date of Patent: Mar. 16, 2010

(54) ENTERIC MEDICINAL COMPOSITION FOR ORAL USE

(75) Inventors: Noboru Tatsumi, Higashikagawa (JP); Hidetoshi Hamamoto, Higashikagawa (JP); Masaki Ishibashi, Higashikagawa (JP); Kanako Shiota, Higashikagawa (JP); Sueko Matsumura, Higashikagawa (JP); Keiko Yamasaki, Higashikagawa (JP)

(73) Assignee: MEDRX Co., Ltd., Kagawa (JP)

( * ) Notice: Subject to any disclaimer, the term of this patent is extended or adjusted under 35 U.S.C. 154(b) by 91 days.

(21) Appl. No.: 11/921,438

(22) PCT Filed: Nov. 4, 2005

(86) PCT No.: PCT/JP2005/020316

§ 371 (c)(1),
(2), (4) Date: Dec. 3, 2007

(87) PCT Pub. No.: WO2006/129386

PCT Pub. Date: Dec. 7, 2006

(65) Prior Publication Data

US 2008/0161364 A1 Jul. 3, 2008

(30) Foreign Application Priority Data

Jun. 3, 2005 (JP) ............................. 2005-163875

(51) Int. Cl.
*A61K 31/4402* (2006.01)
(52) U.S. Cl. ..................................... 514/352
(58) Field of Classification Search ................. None
See application file for complete search history.

(56) References Cited

U.S. PATENT DOCUMENTS

2003/0175335 A1 9/2003 Scott et al.
2005/0037081 A1 2/2005 Eccleston et al.
2005/0089577 A1 4/2005 Yokoyama et al.
2005/0180962 A1* 8/2005 Raz et al. ................. 424/93.45
2005/0249716 A1 11/2005 Bourgeois et al.

FOREIGN PATENT DOCUMENTS

| | | |
|---|---|---|
| JP | 58-172313 | 10/1983 |
| JP | 61-207328 | 9/1986 |
| JP | 4-27352 | 1/1992 |
| JP | 4-258260 | 9/1992 |
| JP | 2000-63289 | 2/2000 |
| JP | 2004-2320 | 1/2004 |
| JP | 2004-507581 | 3/2004 |
| JP | 2004-173675 | 6/2004 |
| JP | 2005-507408 | 3/2005 |
| JP | 2005/325081 | 11/2005 |
| WO | 02/15878 | 2/2002 |
| WO | 2004/016248 | 2/2004 |

OTHER PUBLICATIONS

International Search Report issued Jan. 31, 2006 in the International (PCT) Application PCT/JP2005/020316 of which the present application is the U.S. National Stage.
Marianne Ashford et al., "Studies on pectin formulations for colonic drug delivery", Journal of Controlled Release, 30, pp. 225-232, 1994.
Th. F. Vandamme et al., "The use of polysaccharides to target drugs to the colon", Carbohydrate Polymers, 48, pp. 219-231, 2002.
V.R. Sinha et al., "Polysaccharids in colon-specific drug delivery", International Journal of Pharmaceutics, 224, pp. 19-38, 2001.
Edited by Osaka Hospital Pharmacist Association, Iyakuhin Yoran 5th edition Tsuiho Shusaiban, Kabushiki Kaisha Yakugyo Jihosha, pp. 2126-2127, 1995.

* cited by examiner

*Primary Examiner*—Phyllis G. Spivack
(74) *Attorney, Agent, or Firm*—Wenderoth, Lind & Ponack, L.L.P.

(57) ABSTRACT

An enteric medicinal composition comprising a drug ingredient, pectin, alginic acid, or a derivative thereof, and water is provided that is easy to swallow.

6 Claims, No Drawings

ENTERIC MEDICINAL COMPOSITION FOR ORAL USE

TECHNICAL FIELD

The present invention relates to an enteric medicinal composition for oral dosing.

BACKGROUND ART

An enteric preparation is widely known as one of DDS technologies concerning pharmaceuticals for oral dosing.

An enteric preparation is designed to achieve medical effect by enteric absorption without releasing the drug ingredient in the stomach. By suppressing release of the drug ingredient in the stomach, decomposition of the drug ingredient by gastric acid is prevented and incidence of adverse drug reactions in the stomach is decreased. As a result, it is become possible to increase availability of the drug ingredient.

In general, pH in the stomach is from 1.2 to 3.5, while pH in the intestine is from 5 to 8. Therefore, it is known that an enteric preparation which does not dissolve under the pH in the stomach but dissolves under the pH in the intestine can be produced utilizing the difference in the pH values.

As such an enteric preparation, tablets and capsules have widely been developed heretofore. In these preparations, a coating layer is formed using an enteric base ingredient on a nucleus containing a drug ingredient, or a matrix is formed using the enteric base ingredient and a drug ingredient.

However, water is required for taking a tablet or capsule. Even in case that these preparations are taken together with water, these are difficult to be swallowed when their size is large. In addition, swallowing a capsule is sometimes difficult, since it easily adheres to mucous membrane. Particularly, it is difficult for infants and elderly people to take a table and capsule, because their swallowing function is inferior.

On the other hand, a gel and jelly can be taken with favorable feelings. Accordingly, a technology using polysaccharide having gelation function and thickening effect has been developed.

For example, Japanese Unexamined Patent Publication No. 2004-173675 discloses a technology that bacteria are enclosed in a solid which is hardened with a coagulating agent, and the bacteria are taken alive into the intestine. As the coagulating agent, pectin and alginic acid are described, however, these are just merely exemplified. Further, this technology is not a one for releasing a drug ingredient in the intestine.

Japanese Unexamined Patent Publication No. 4-258260 discloses a polysaccharide gel and a polysaccharide gel composition, which are prepared by forcible hydration of polysaccharide such as pectin and alginate under a high pressure treatment. In the publication, a calcium-rich alginic acid gel is exemplified as an enteric gel. The gel is a dietary food, which separates into calcium and alginic acid in the stomach and allows calcium to be absorbed in the intestine. Namely, the gel is not for releasing a drug ingredient in the intestine.

Japanese Unexamined Patent Publication No. 4-27352, Japanese Unexamined Patent Publication No. 61-207328 and Japanese Unexamined Patent Publication No. 58-172313 disclose enteric soft capsules using pectin or alginate. These are technologies for making a film of the soft capsule or for coating a surface of the soft capsule using polysaccharide such as pectin and alginate. In addition, pectin and alginate are just merely exemplified as an enteric polysaccharide.

Japanese Unexamined Patent Publication No. 2004-507581 discloses a film composition in which pectin is used as an enteric material. The composition is used as a base material of a hard capsule.

Further, WO2002/015878 discloses an aqueous suspension containing a hardly-soluble drug, polyvinyl pyrolidone and a water-soluble anionic polymer. The technology is simply for stably dispersing the drug in an aqueous solution, and there is no description of enteric property at all in the document.

DISCLOSURE OF THE INVENTION

As described above, there has never been obtained a pharmaceutical product which has an enteric property and is easy to be swallowed for a patient.

The present invention was developed in consideration of the above circumstances, and an object of the present invention is to provide a medicinal composition which has both of enteric property and dosing property.

The present inventors have intensively studied to achieve the above object. As a result, the present inventors found that the composition prepared by dissolving pectin and alginic acid or derivative thereof in water exhibits an enteric property and is also excellent in a dosing property. Thus, the present invention was completed.

The enteric medicinal composition of the present invention, which can achieve the above object, is characterized by comprising a drug ingredient, pectin, alginic acid or derivative thereof, and water.

A total content of the pectin and the alginic acid or derivative thereof is preferably from 0.1 to 10% by mass in a total amount of the medicinal composition. Such a medicinal composition can be sufficiently gelled, and also hardness and viscosity of the gel can be more proper.

The enteric medicinal composition is preferably gel. With this drug form, the medicinal composition can be swallowed much more easily, and it becomes possible to further improve the dosing property.

It is preferred that the drug ingredient is salazosulfapyridine. The medicinal composition fully suppresses the release of salazosulfapyridine in the stomach, and it becomes possible to further exhibit its drug efficacy.

BEST MODE FOR CARRYING OUT THE INVENTION

The present inventors have intensively studied formulation using pectin and alginic acid or derivative thereof. As a result, the present inventors have confirmed that pectin and alginic acid or derivative thereof are gelled under the condition of low pH, which corresponds to the environment in the stomach, and are rapidly dissolved in an aqueous solution of pH 6 to 8, which corresponds to the environment in the intestine. The present inventors also found that a single use of either pectin or these alginic acids exhibits insufficient acid resistance, and the acid resistance is improved by further using pectin and these alginic acids in combination. Thus, the present invention has been completed.

The enteric medicinal composition of the present invention is characterized by comprising a drug ingredient, pectin, alginic acid or derivative thereof, and water.

Pectin used in the present invention is a polysaccharide composed of galacturonic acid and methyl ester thereof, which is extracted from plants such as apple. According to the esterification degree, pectin is classified into a low methoxyl (LM) pectin and a high methoxyl (HM) pectin. It is preferred to use HM pectin as the pectin of the present invention, because HM pectin is more likely to be gelled even under a low pH condition, and thus enteric property and dosing property of the medicinal composition are further improved.

The amount of the pectin in the medicinal composition is preferably from 0.02 to 10% by mass, more preferably from 0.05 to 5% by mass, and most preferably from 0.08 to 1% by mass. In case that the amount is 0.02% by mass or more, the medicinal composition is sufficiently gelled. When the amount is 10% by mass or less, it may be enabled to prevent the gel from being too hard or too high in viscosity, in other words, the enteric property and dosing property of the medicinal composition are further improved.

Example of alginic acid or derivative thereof used in the present invention includes alginic acid, metal salt thereof and ester thereof. The alginic acid is a linear acidic polysaccharide, which is extracted from seaweeds and microorganisms, and is composed of glucuronic acid and mannuronic acid. Among them, the metal salt is preferable, and example thereof includes sodium alginate, calcium alginate, potassium alginate and ammonium alginate. Among them, sodium alginate is more preferable.

The amount of the alginic acid or derivative thereof to be mixed in the medicinal composition is preferably from 0.02 to 10% by mass, more preferably from 0.05 to 5% by mass, and most preferably from 0.08 to 1% by mass. In case that the amount is 0.02% by mass or more, the composition can be sufficiently gelled. When the amount is 10% by mass or less, it may be enabled to prevent the gel from being too hard or too high in viscosity, in other words, the enteric property and dosing property of the medicinal composition are further improved.

The total amount of the pectin and the alginic acid or derivative thereof is preferably from 0.1 to 10% by mass, and more preferably from 0.15 to 5% by mass, and most preferably from 0.2 to 2% by mass. In case that the amount is 0.1% by mass or more, the composition can be sufficiently gelled. When the amount is 10% by mass or less, it may be enabled to prevent the gel from being too hard or too high in viscosity, in other words, the enteric property and dosing property of the medicinal composition are further improved.

The mixing ratio of the pectin and the alginic acid or derivative thereof can be properly determined within a range of the amount and the total amount of the pectin and the alginic acid or derivative thereof. However, in view of further improving the enteric property and dosing property, the ratio of the alginic acid or derivative thereof to the pectin is preferably from 0.1 to 10, more preferably from 0.2 to 5, and most preferably from 0.4 to 2.5, when the ratio of the pectin is defined as 1.

Although the drug ingredient used in the present invention is not particularly limited as long as the drug ingredient is applicable to an enteric preparation, for example, a hardly-soluble drug having a basic group is preferred. In case that the present invention is applied to a drug ingredient whose solubility under an acidic condition is low, the release of the drug ingredient in the stomach can be more suppressed, and thus, it is enable to further increase effectiveness as an enteric preparation. As such a drug ingredient, salazosulfapyridine is particularly preferred.

The amount of the drug ingredient in the total amount of the medicinal composition is not particularly limited. The amount of the drug ingredient may be an amount that is necessary for achieving medical effect, and it differs depending on a kind of the drug ingredient. However, in view of further excellence in the enteric property and dosing property of the medicinal composition of the present invention, the amount is preferably 40% by mass or less, more preferably 30% by mass or less, and most preferably 20% by mass or less. On the other hand, the lower limit of the amount is determined in accordance with the effective dose of the drug ingredient, and so is not limited. However, the lower limit is preferably 0.01% by mass or more, more preferably 0.1% by mass, and most preferably 1% by mass.

Water used in the present invention is not particularly limited so long as the water can be used for pharmaceutical use. For example, purified water, distilled water or the like can be used. The amount of water to be mixed can be appropriately adjusted such that the total of water and the other ingredients is 100% by mass.

To the enteric medicinal composition of the present invention, other additives can be added if necessary, in addition to the above additives. Examples thereof include base material (for example, water-soluble polymers such as carboxy vinyl polymer, xanthan gum, carrageenan, carob bean gum, starch acrylate, sodium polyacrylate, polyvinyl alcohol, carmellose sodium; glycerin; macrogol; silicic anhydride), diluent base (for example, starch derivatives such as dextrin; cellulose derivatives such as carmellose sodium; water-soluble polymers such as xanthan gum), colorant, lubricant (for example, metal stearate salts such as calcium stearate, magnesium stearate; lauryl sulfate salts such as sodium lauryl sulfate, calcium lauryl sulfate; starch derivative in the above diluent base), corrigent (for example, saccharides such as sugar; sugar alcohols such as D-sorbitol; artificial sweeteners such as aspartame, saccharin sodium; protein sweeteners such as thaumatin), emulsifier, thickener, humectant, stabilizer (for example, parahydroxybenzoic esters such as methyl paraben, ethyl paraben, propyl paraben; alcohols such as chlorobutanol, benzyl alcohol, phenylethyl alcohol; benzalkonium chloride; phenol; phenols such as cresol; acetic anhydride; sorbic acid), preservative, solvent (for example, water, propylene glycol, butylene glycol, isopropanol, ethanol, glycerin, diethyl sebacate, isopropyl myristate, diisopropyl adipate, myristyl palmitate, stearyl stearate, myristyl myristate, seryl lignocerate, lacceryl cerotate, lacceryl laccerate), solubilizing agent, suspending agent (for example, carmellose sodium), antioxidant (for example, sodium hydrogen sulfite, L-ascorbic acid, sodium ascorbate, butylhydroxyanisol, butylhydroxytoluene, propyl gallate, tocophenol acetate, dl-α-tocophenol), adjuvant remedy (for example, peppermint oil, 1-menthol, camphor, thymol, glycyl retinoic acid, nonylic acid vanilyl amide, capsaicin extract), buffer, pH adjuster (for example, organic acids and organic acid salts such as citric acid, malic acid, tartaric acid, succinic acid, lactic acid, acetic acid and the metal salts thereof; amines such as triethanolamine, triisopropanolamine, ethanolamine; inorganic bases and salts such as sodium hydroxide, potassium hydroxide, calcium hydroxide, magnesium hydroxide, carbonic acid, sodium carbonate, phosphoric acid, metal phosphate, hydrochloric acid, sulfuric acid). The amount of these additives to be mixed can be appropriately adjusted according to need, so long as the effect of the present invention is not adversely affected.

The enteric medicinal composition of the present invention is not particularly limited as long as the composition has a preparation form containing water. For example, a gel (also called as "jellied") preparation is preferred, because such a preparation is easy to be swallowed even for those who have difficulty in swallowing, so it becomes easy to get compliance, and the effectiveness of the drug ingredient can be further sufficiently exhibited. In addition, such a gel preparation excels in handling property and is easy to be taken out from a container.

Hereinafter, the present invention will be described more in detail with reference to Examples; however it is not intended that the present invention be limited to the following Examples, and modifications and substitutions to the Examples can be made without departing from the intent of the anteroposterior description. Such modifications and substitutions are included in the technical scope of the present invention.

EXAMPLES

Preparation Examples 1 and 2

Gel preparations containing salazosulfapyridine were prepared according to the formulation shown in Table 1. Specifically, salazosulfapyridine, saccharin sodium, D-sorbitol, citric acid, sodium citrate, propyl paraoxybenzoate and polyvinyl alcohol were dispersed or dissolved in purified water. While the mixture was stirred, a dispersion solution prepared by dispersing pectin, sodium alginate and xanthan gum in glycerin or propylene glycol was slowly added. After a perfume was further added, the stirred mixture solution was heated to a temperature of 70 to 95° C. Then, the mixture was dispensed in containers while the mixture was warm. The dispensed mixture was cooled naturally to prepare medicinal gel compositions of Preparation Examples 1 and 2.

Preparation Examples 3 to 9

Gel preparations containing salazosulfapyridine were prepared according to the formulation shown in Table 2 and Table 3. Specifically, salazosulfapyridine, saccharin sodium, thaumatin, D-sorbitol, citric acid, sodium citrate, methyl paraoxybenzoate, ethyl paraoxybenzoate, propyl paraoxybenzoate and polyvinyl alcohol were dispersed or dissolved in purified water. While the mixture was stirred, a dispersion solution prepared by dispersing pectin, sodium alginate, carrageenan, carob bean gum and xanthan gum in glycerin or propylene glycol was slowly added. After a perfume was further added, the stirred mixture solution was heated to a temperature of 70 to 95° C. Then, the mixture was dispensed in containers while the mixture was warm. The dispensed mixture was cooled naturally to prepare medicinal gel compositions of Preparation Examples 3 to 9.

TABLE 1

| Name of raw materials | Preparation Example 1 | Preparation Example 2 |
|---|---|---|
| Salazosulfapyridine | 12.5 | 12.5 |
| Saccharin sodium | 0.1 | 0.2 |
| D-sorbitol | 30.0 | 35.0 |
| Citric acid | 0.6 | 0.5 |
| Sodium citrate | 0.1 | 0.1 |
| Propyl paraoxybenzoate | 0.05 | 0.05 |
| Polyvinyl alcohol | 0.7 | 0.7 |
| Pectin | 0.7 | 0.7 |
| Sodium alginate | 0.8 | 0.9 |
| Xanthan gum | 0.1 | — |
| Glycerin | 5.0 | — |
| Propylene glycol | — | 5.0 |
| Perfume | Trace amount | Trace amount |
| Purified water | Balance | Balance |
| Total | 100 | 100 |

Unit: % by mass

TABLE 2

| Name of raw materials | Preparation Example 3 | Preparation Example 4 | Preparation Example 5 | Preparation Example 6 |
|---|---|---|---|---|
| Salazosulfapyridine | 14.3 | 14.3 | 14.3 | 14.3 |
| Saccharin sodium | 0.1 | 0.1 | 0.1 | 0.1 |
| Thaumatin | — | — | — | — |
| D-sorbitol | 30.0 | 30.0 | 30.0 | 30.0 |
| Citric acid | 0.08 | 0.08 | 0.08 | 0.08 |
| Sodium citrate | 0.5 | 0.5 | 0.5 | 0.5 |
| Ethyl paraoxybenzoate | 0.02 | 0.02 | 0.02 | 0.02 |
| Methyl paraoxybenzoate | 0.04 | 0.04 | 0.04 | 0.04 |
| Polyvinyl alcohol | 0.7 | 0.7 | 0.7 | 0.7 |
| Pectin | 0.2 | 0.5 | 0.1 | — |
| Sodium alginate | 0.2 | — | — | — |
| Carrageenan | 0.58 | 0.58 | 0.58 | 0.58 |
| Carob bean gum | 0.18 | 0.18 | 0.18 | 0.18 |
| Xanthan gum | — | — | — | — |
| Glycerin | 9.0 | 9.0 | 9.0 | 9.0 |
| Propylene glycol | — | — | — | — |
| Perfume | Trace amount | Trace amount | Trace amount | Trace amount |
| Purified water | Balance | Balance | Balance | Balance |
| Total | 100 | 100 | 100 | 100 |

Unit: % by mass

TABLE 3

| Name of raw materials | Preparation Example 7 | Preparation Example 8 | Preparation Example 9 |
|---|---|---|---|
| Salazosulfapyridine | 14.3 | 14.3 | 14.3 |
| Saccharin sodium | 0.1 | 0.1 | 0.1 |
| Thaumatin | Trace amount | — | — |
| D-sorbitol | 30.0 | 30.0 | 30.0 |
| Citric acid | 0.08 | 0.08 | 0.08 |
| Sodium citrate | 0.5 | 0.5 | 0.5 |
| Ethyl paraoxybenzoate | 0.04 | 0.04 | 0.04 |
| Propyl paraoxybenzoate | 0.02 | 0.02 | 0.02 |
| Polyvinyl alcohol | 0.7 | 0.7 | 0.7 |
| Pectin | 0.2 | — | — |
| Sodium alginate | 0.2 | 0.5 | 0.1 |
| Carrageenan | 0.58 | 0.58 | 0.58 |
| Carob bean gum | 0.18 | 0.18 | 0.18 |
| Xanthan gum | — | — | — |
| Glycerin | 9.0 | 9.0 | 9.0 |
| Propylene glycol | — | — | — |
| Perfume | Trace amount | Trace amount | Trace amount |
| Purified water | Balance | Balance | Balance |
| Total | 100 | 100 | 100 |

Unit: % by mass

Test Example 1

Disintegration Test

The test was conducted in accordance with Dissolution Test Part 2 described in Japan Pharmacopoeia, and disintegration state and releasing state of the medicinal compositions prepared in Preparation Examples 1 to 9 were confirmed. The test conditions were as follows; Test solution: first fluid of Disintegration Test described in Japan Pharmacopoeia (pH 1.2) 900 ml, solution temperature: 37° C., revolution number of paddle: 50 revolutions/minute, amount to be charged: about 3.5 g. Disintegration state and releasing state of the medicinal compositions were visually observed after 5, 10, 15, 30, 60, 90 and 120 minutes of elapsed time from the beginning of the test. The same test was conducted with respect to a commercially available salazosulfapyridine enteric tablet. The results are shown in Tables 4 to 6.

TABLE 4

| | | Time (minutes) | | | | | | |
|---|---|---|---|---|---|---|---|---|
| | | 5 | 10 | 15 | 30 | 60 | 90 | 120 |
| Disintegration of the preparation | Preparation Example 1 | Not Observed | Not Observed | Not Observed | Not Observed | Not Observed | Not Observed | Not Observed |
| | Commercially available tablet | Not Observed | Not Observed | Not Observed | Not Observed | Not Observed | Not Observed | Not Observed |
| Release of the drug | Preparation Example 2 | Not Observed | Not Observed | Not Observed | Not Observed | Not Observed | Not Observed | Not Observed |
| | Commercially available tablet | Not Observed | Not Observed | Not Observed | Not Observed | Not Observed | Not Observed | Not Observed | n = 4-5

TABLE 5

| | | Time (minutes) | | | | | | |
|---|---|---|---|---|---|---|---|---|
| | | 5 | 10 | 15 | 30 | 60 | 90 | 120 |
| Disintegration of the preparation | Preparation Example 3 | Not observed | Not observed | Not observed | Not observed | Not observed | Not observed | Not observed |
| | Preparation Example 4 | Observed | Observed | Observed | Observed | Observed | Observed | Observed |
| | Preparation Example 5 | Observed | Observed | Observed | Observed | Observed | Observed | Observed |
| | Preparation Example 6 | Observed | Observed | Observed | Observed | Observed | Observed | Observed |
| | Commercially available tablet | Not observed | Not observed | Not observed | Not observed | Not observed | Not observed | Not observed |
| Release of the drug | Preparation Example 3 | Not observed | Not observed | Not observed | Not observed | Not observed | Not observed | Not observed |
| | Preparation Example 4 | Observed | Observed | Observed | Observed | Observed | Observed | Observed |
| | Preparation Example 5 | Observed | Observed | Observed | Observed | Observed | Observed | Observed |
| | Preparation Example 6 | Observed | Observed | Observed | Observed | Observed | Observed | Observed |
| | Commercially available tablet | Not observed | Not observed | Not observed | Not observed | Not observed | Not observed | Not observed | n = 3-4

TABLE 6

| | | Time (minutes) | | | | | | |
|---|---|---|---|---|---|---|---|---|
| | | 5 | 10 | 15 | 30 | 60 | 90 | 120 |
| Disintegration of the preparation | Preparation Example 7 | Not observed | Not observed | Not observed | Not observed | Not observed | Not observed | Not observed |
| | Preparation Example 8 | Not observed | Not observed | Not observed | Not observed | Not observed | Observed | Observed |
| | Preparation Example 9 | Not observed | Not observed | Not observed | Not observed | | Observed | Observed |
| | Commercially available tablet | Not observed | Not observed | Not observed | Not observed | Not observed | Not observed | Not observed |

TABLE 6-continued

|  |  | Time (minutes) | | | | | | |
| --- | --- | --- | --- | --- | --- | --- | --- | --- |
|  |  | 5 | 10 | 15 | 30 | 60 | 90 | 120 |
| Release of the drug | Preparation Example 7 | Not observed | Not observed | Not observed | Not observed | Not observed | Not observed | Not observed |
|  | Preparation Example 8 | Not observed | Not observed | Not observed | Not observed | Not observed | Not observed | Not observed |
|  | Preparation Example 9 | Not observed | Not observed | Not observed | Not observed | Observed | Observed | Observed |
|  | Commercially available tablet | Not observed | Not observed | Not observed | Not observed | Not observed | Not observed | Not observed | n = 3-4

As is apparent from the results shown in Table 4 to 6, it was confirmed that the medicinal compositions of Preparation Examples 1 to 3 and 7 which satisfied the requirements of the present invention did not disintegrate in the test solution of pH 1.2 even after 120 minutes, and salazosulfapyridine remained in the medicinal compositions without being released. Further, it was confirmed that the disintegration state and releasing state were similar to those of a commercially available enteric tablet.

On the other hand, it was confirmed that the medicinal compositions of Preparation Examples 4 to 6, 8 and 9 which did not satisfy the requirements of the present invention disintegrated or released salazosulfapyridine by a lapse of 90 minutes.

As a result, it was found that a combination of pectin and alginic acid or derivative thereof enables further improvement of acid resistance as compared with the case where pectin is used alone, or alginic acid or derivative thereof is used alone.

Test Example 2

Dissolution Test

The elution behavior of salazosulfapyridine in Preparation Examples 1, 3, 4, 8 and 9 was examined under similar test conditions to Test Example 1, except that a buffer solution of citric acid-phosphate adjusted to pH 6.8 was used as the test solution and the absorbance of salazosulfapyridine was measured at each elapsed point to calculate the elution rate. The elution behavior of the commercially available salazosulfapyridine enteric tablet was also examined in a similar manner. The results are shown in Tables 7 and 8.

TABLE 7

|  |  | Time (minutes) | | | | | | |
| --- | --- | --- | --- | --- | --- | --- | --- | --- |
|  |  | 5 | 10 | 15 | 30 | 60 | 90 | 120 |
| Dissolution ratio (%) | Preparation Example 1 | 9 | 24 | 36 | 71 | 101 | 104 | 105 |
|  | Commercially available tablet | 1 | 9 | 29 | 84 | 99 | 102 | 105 | n = 3-4

TABLE 8

|  |  | Time (minutes) | | | | | | |
| --- | --- | --- | --- | --- | --- | --- | --- | --- |
|  |  | 5 | 10 | 15 | 30 | 60 | 90 | 120 |
| Dissolution ratio (%) | Preparation Example 3 | 10 | 23 | 36 | 68 | 99 | 103 | 105 |
|  | Preparation Example 4 | 7 | 19 | 33 | 68 | 99 | 104 | 106 |
|  | Preparation Example 7 | 8 | 20 | 33 | 65 | 97 | 105 | 105 |
|  | Preparation Example 8 | 7 | 19 | 32 | 66 | 98 | 102 | 106 |
|  | Preparation Example 9 | 10 | 24 | 39 | 73 | 101 | 104 | 107 |
|  | Commercially available tablet | 0.1 | 6 | 30 | 83 | 95 | 98 | 101 | n = 3-4

As is apparent from the results shown in Tables 7 and 8, the elution behavior of salazosulfapyridine contained in each medicinal composition of all Preparation Examples after 15 minutes was almost the same as that of a commercially available enteric tablet in the test solution of pH 6.8.

The above results revealed that the medicinal compositions which satisfied the requirements of the present invention were free from disintegration and releasing at pH 1.2 for 120 minutes, while the drug ingredient is eluted at pH 6.8, and the behavior of the composition was almost the same as that of a commercially available enteric tablet.

Accordingly, the medicinal composition of the present invention has enough drug release property as a enteric preparation. Also, since the medicinal composition of the present invention is gel, it is easier to take the medicinal composition than a tablet or capsule. It is also possible to take the medicinal composition without water and thus the medicinal composition of the present invention is excellent in dosing property.

INDUSTRIAL APPLICABILITY

The enteric medicinal composition of the present invention exhibits an enteric property, and is also excellent in a dosing property. Accordingly, by the present invention, it becomes easier to take an enteric preparation which has been not easily swallowed. Therefore, it can be easier to get compliance from those who take the drug, and the present invention will greatly contribute to further enhancement of drug efficacy. Since it becomes possible for infants and elderly people whose swallowing function is inferior to take a drug easily, mental and physical affliction that guardians and caretakers suffer from in a domestic, medical or welfare scene can be greatly alleviated. Since those who take a drug are also relieved from the difficulty of swallowing the drug, the medicinal composition of the present invention will serve for improving quality of their life.

The invention claimed is:

1. An enteric medicinal composition, comprising a drug ingredient, pectin, alginic acid or derivative thereof, and water,
   wherein the enteric medicinal composition is a gel,
   a total content of the pectin and the alginic acid or derivative thereof is from 0.1 to 10% by mass in a total amount of the enteric medicinal composition,
   a ratio of the alginic acid or derivative thereof to the pectin is from 0.2 to 5,
   the alginic acid or derivative thereof is alginic acid, sodium alginate, calcium alginate, potassium alginate, or ammonium alginate,
   the enteric medicinal composition is free both from disintegration and from releasing the drug ingredient at pH 1.2 for 120 minutes, and
   the drug ingredient is eluted at pH 6.8.

2. The enteric medicinal composition according to claim 1, wherein the drug ingredient is salazosulfapyridine.

3. The enteric medicinal composition according to claim 1, wherein a content of the drug ingredient is from 0.01 to 40% by mass in the total amount of the medicinal composition.

4. The enteric medicinal composition according to claim 1, wherein the alginic acid or derivative thereof is sodium alginate.

5. The enteric medicinal composition according to claim 1, wherein the total content of the pectin and the alginic acid or derivative thereof is from 0.2 to 2% by mass in the total amount of the medicinal composition.

6. The enteric medicinal composition according to claim 1, wherein the ratio of the alginic acid or derivative thereof to the pectin is from 0.4 to 2.5.

* * * * *